(12) United States Patent
Campagna et al.

(10) Patent No.: US 8,544,471 B2
(45) Date of Patent: *Oct. 1, 2013

(54) APPARATUS AND METHOD FOR RADIOLUCENT ANATOMIC POSITIONING

(75) Inventors: Michael Campagna, Oak Park, IL (US); Jonathan S. Citow, Glencoe, IL (US)

(73) Assignee: Design MD LLC., Libertyville, IL (US)

( * ) Notice: Subject to any disclaimer, the term of this patent is extended or adjusted under 35 U.S.C. 154(b) by 308 days.

This patent is subject to a terminal disclaimer.

(21) Appl. No.: 12/684,934

(22) Filed: Jan. 9, 2010

(65) Prior Publication Data

US 2010/0179604 A1    Jul. 15, 2010

Related U.S. Application Data

(63) Continuation-in-part of application No. 11/315,060, filed on Dec. 22, 2005, now Pat. No. 7,669,602.

(51) Int. Cl.
*A61G 15/00* (2006.01)
(52) U.S. Cl.
USPC .......................................... 128/845; 378/208

(58) Field of Classification Search
USPC .................. 128/845; 378/180, 195, 204, 208
See application file for complete search history.

(56) References Cited

U.S. PATENT DOCUMENTS

| | | |
|---|---|---|
| 3,759,252 A | 9/1973 | Berman |
| 3,993,088 A | 11/1976 | Thomas |
| 4,183,520 A | 1/1980 | Chase |
| 4,456,248 A | 6/1984 | Smith |
| 5,011,216 A | 4/1991 | Baughman |
| 6,168,548 B1 | 1/2001 | Fleming |
| 6,820,621 B2 | 11/2004 | DeMayo |
| 2007/0144530 A1 | 6/2007 | McGinnis et al. |

*Primary Examiner* — Patricia Bianco
*Assistant Examiner* — Camtu Nguyen
(74) *Attorney, Agent, or Firm* — Ariel S. Bentolila; Bay Area IP Group, LLC

(57) ABSTRACT

An apparatus and method includes a first anatomic positioner for migrating a first anatomic part. The first anatomic positioner includes a first tapered arm for applying a motive force and a first arch at a distal end of the first tapered arm for contacting the first anatomic part. The first arch includes a varying width and a varying density where the first arch is asymmetrically offset from the first tapered arm such that a longitudinal axis of the first tapered arm extends through a lower portion of the first arch.

23 Claims, 2 Drawing Sheets

Section AA

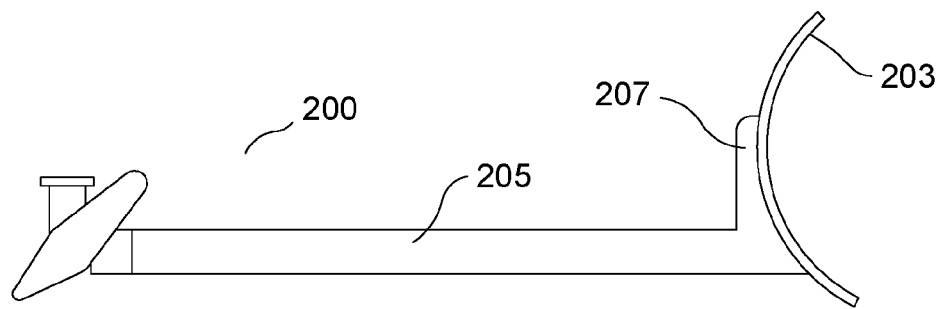
Figure 2
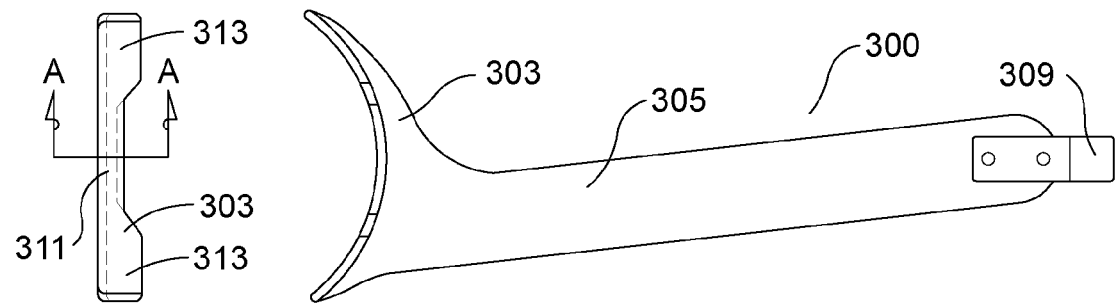
Figure 3A
Section AA
Figure 3C
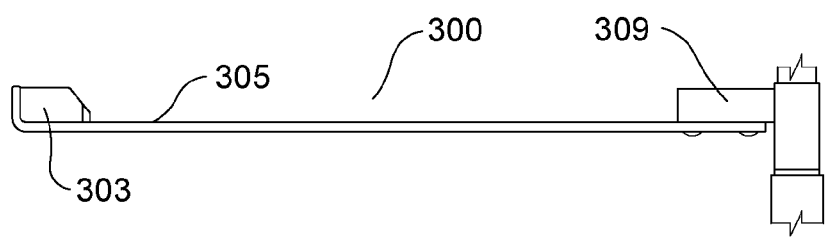
Figure 3B

APPARATUS AND METHOD FOR RADIOLUCENT ANATOMIC POSITIONING

CROSS-REFERENCE TO RELATED APPLICATIONS

The present continuation-in-part patent application claims priority benefit of the U.S. nonprovisional patent application Ser. No. 11/315,060 filed on Dec. 22, 2005 now U.S. Pat. No. 7,669,602 under 35 U.S.C. 120 and entitled "Shoulder Press", which is hereby incorporated by reference for all purposes.

RELATED CO-PENDING U.S. PATENT APPLICATIONS

The following related U.S. patent application(s), submitted by at least one of the present Applicant(s)/Inventor(s) is/(are) recently co-pending:
U.S. utility patent application Ser. No. 12/464,456 filed on 12 May 2009 and entitled "AN APPARATUS FOR MOUNTING AN ANATOMICAL POSITIONER ON A PATIENT CARE PLATFORM"; and, U.S. utility patent application Ser. No. 13/098,293 filed on 29 Apr. 2011 and entitled Apparatus for Radiolucent Patient Positioning and Method of Using the Apparatus; and Ser. No. 13/174,652 filed on 30 Jun. 2011 and entitled "Apparatus for Migrating Anatomic Parts and Method of Using the Apparatus"; and Ser. No. 13/174,703 filed on 30 Jun. 2011 and entitled "Apparatus and Method for Migrating Anatomic Parts".

FEDERALLY SPONSORED RESEARCH OR DEVELOPMENT

Not applicable.

REFERENCE TO SEQUENCE LISTING, A TABLE, OR A COMPUTER LISTING APPENDIX

Not applicable.

COPYRIGHT NOTICE

A portion of the disclosure of this patent document contains material that is subject to copyright protection. The copyright owner has no objection to the facsimile reproduction by anyone of the patent document or patent disclosure as it appears in the Patent and Trademark Office, patent file or records, but otherwise reserves all copyright rights whatsoever.

FIELD OF THE INVENTION

The present invention relates generally to medical equipment. More particularly, the invention relates to means for rigid radiolucent anatomic positioning that alleviates density artifact while maintaining strength.

BACKGROUND OF THE INVENTION

Medical procedures involving the cervical spine, particularly surgery, require correct visualization of the vertebrae during radiography (e.g., X-Ray, fluoroscopy, CT, MRI). Typically, a subject's shoulders obscure the lateral imaging of the cervical vertebrae. It is therefore an objective of the present invention to provide means for positioning the subject's shoulders during radiography that migrate the shoulders out of the line of sight of the lateral image of the cervical vertebrae.

Traditionally, said migration of a subject's shoulders is effected via the following means. One traditional method of migrating the subject's shoulders involves Kurlix Bandages that are wrapped around the forearms or wrists of the subject and pulled upon forcefully during live radiography for the purpose of temporary distal migration of the shoulder structures. This method results in temporary migration of the shoulders and unimpeded radiographic visualization of the cervical vertebral structures. However, this method may also result in injury for example, without limitation, Brachial Plexus injury or insult to the subject's shoulder capsule due to over-application of distal migratory force. Another traditional method of moving the subject's shoulders involves taping down the subject's shoulder's and trapezius muscles for the entirety of the procedure. Using this method, the shoulders migrate for the entirety of the procedure allowing for unimpeded radiographic visualization of the cervical vertebral structures. However, some unintended results of this method includes incidence of, without limitation, sore trapezius, nerve damage, tingling hands, reduced digital sensation, and numbness for the subject upon awakening as a consequence of extended unnatural positioning for the entirety of the procedure.

Currently, almost all anatomic positioning for purposes of radiography is performed with foam, which is radiolucent and sufficient to position and fixate portions of the anatomy for example, without limitation, supporting a raised head or immobilizing the head into a certain position. However, foam is incapable of being utilized to migrate portions of the anatomy for example, without limitation, moving and holding the shoulders. Foam lacks the mechanical rigidity and strength needed to migrate portions of the anatomy and merely compresses when subjected to motive pressure. For purposes of variable migration and placement of portions of the anatomy, it is necessary to utilize a rigid radiolucent structure, as opposed to a soft structure. This is much more difficult than one would suppose. The difficulty lies in the actual manufacture of a rigid radiolucent positioning device that is strong enough and radiolucent enough. An object is radiolucent if it creates little interference with the X-Rays or other types of radiography. Except for various "halo" style radiolucent head positioners designed specifically for the fixation of the head during surgery, as opposed to variable positioning or migration, at present there do not exist means for rigid radiolucent anatomic positioning other than a shoulder pusher.

THE Shoulder Pusher is a rigid radiolucent positioning device utilized for migrating the shoulders. The Shoulder Pusher is a radiolucent U shaped member that is positioned on the shoulders to transmit motive force. However, the structure of this device does not have a method of construction that can accomplish this feat effectively. The difficulty of construction of such a device stems from the occurrence of an artifact, which refers to the obscuration of radiography via structural density. Dense objects cause an opaque shadow during X-ray which obscure a clear view of pertinent structures necessary for diagnostic and intra-operative radiography. Additionally, none of the prior arts which have been cited in reference to the Shoulder Pusher involved any radiolucent function as a pertinent part of their designs. They are all merely simple uniform density arches which shared a simple external appearance to the arch as illustrated in the shoulder pusher. In regards to these prior arts, even if they are constructed from a radiolucent material, they would fail for the same reason the shoulder pusher fails; too much density is generated by the structure. Simply constructing something from radiolucent materials does not render it radiolucent. Furthermore, simply reducing the density of the structures of the shoulder pusher as described does not result in a workable remedy, as it lacks sufficient strength while still directly overlaying the vertebral column.

FIGS. 1A and 1B illustrate an exemplary shoulder pusher 100, in accordance with the prior art. FIG. 1A is a diagrammatic top view, and FIG. 1B is a diagrammatic side view. Shoulder pusher 100 comprises a pair of simple arches 103 of uniform density that are bisected by a pair of simple pusher tubes 105. Pusher tubes 105 are connected by an adjustable connection tube 106. Shoulder pusher 100 provides a means of temporary migration of the shoulders via the hand-held application of bilateral motive force during cervical vertebral radiography for the purpose of obtaining optimized lateral imaging of a subject's cervical vertebral column unimpeded by the unintended imaging of the structures of the subjects shoulders. Arch 103 is permanently attached to pusher tube 105 via a carbon/glue interface 107 at the point of bisection. In that carbon fiber is an essentially brittle material, the thickness and density of arch design are essential for purposes of strength as is the placement of pusher tubes 105 in such a manner as to bisect the circumference of arches 103. In typical use, arches 103 of shoulder pusher are positioned on the subject's shoulders and, when pusher tubes 105 are pushed by an operator, transmit a motive force upon the shoulders, facilitating the transient movement of these structures to visualize an additional two to three vertebrae. Although shoulder pusher 100 actually alleviates some artifact due to a clear view of the cervical vertebral structures via a temporary migration of the shoulders, shoulder pusher 100 concurrently contributes artifact. In fact, surgeons have reported that shoulder pusher 100 actually contributes as much artifact as it alleviates, rendering shoulder pusher 100 a partial, as opposed to complete, improvement over the traditional means of optimization of radiography via migration of the subject's shoulders.

Through study of radiographic views obtained from various surgeons, it has been determined that this artifact originated directly from three specific portions of shoulder pusher 100, resulting in the simultaneous introduction a small yet significant artifact directly in the optimum line of site, even as shoulder pusher 100 alleviated the majority of the artifact caused by the shoulders via migration of the structures of the shoulders. These three causes of artifact are as follows: direct/partial obscuration of the cervical vertebral structures due to line of sight positional overlayment and interference of pusher tube 105 as viewed from the crucial lateral perspective, direct/partial obscuration of the lower vertebral structures by arch 103, and direct/partial obscuration of the critical vertebral structures due to the direct overlayment of carbon/glue interface 107.

In view of the foregoing, there is a need for improved techniques for providing rigid radiolucent anatomic positioning that alleviates line of sight overlayment of the vertebral structures, which reduces or eliminates density artifacts while simultaneously maintaining strength.

BRIEF DESCRIPTION OF THE DRAWINGS

The present invention is illustrated by way of example, and not by way of limitation, in the figures of the accompanying drawings and in which like reference numerals refer to similar elements and in which:

FIG. 1A is a diagrammatic top view, and FIG. 1B is a diagrammatic side view;

FIG. 2 is a diagrammatic side view of an exemplary shoulder pusher, in accordance with an embodiment of the present invention; and FIGS. 3A, 3B and 3C illustrate an exemplary one-piece shoulder pusher, in accordance with an embodiment of the present invention. FIG. 3A is a diagrammatic side view. FIG. 3B is a diagrammatic top view, and FIG. 3C is a diagrammatic front view.

Figure 1:
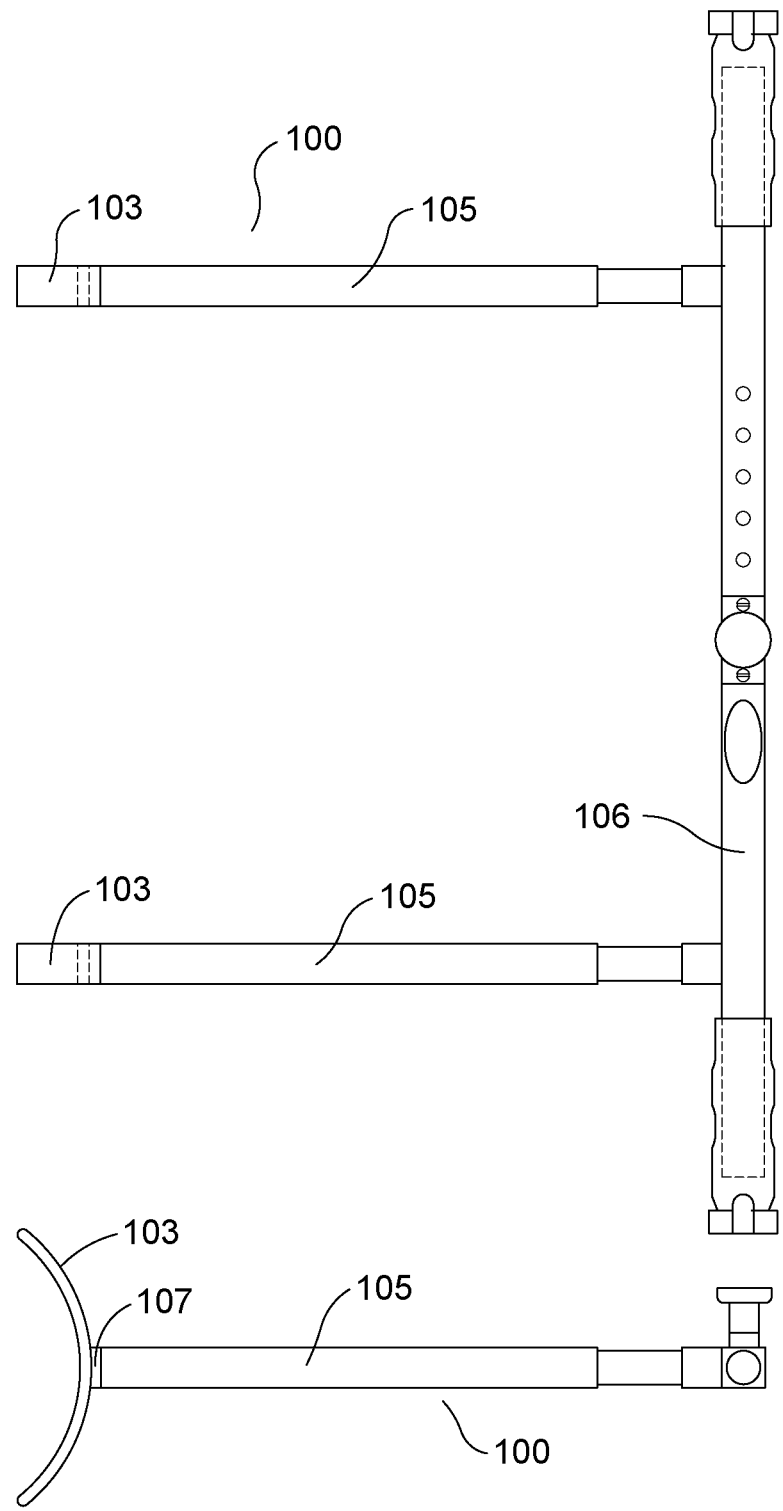
FIGS. 1A and 1B illustrate an exemplary shoulder pusher, in accordance with the prior art.

Unless otherwise indicated illustrations in the figures are not necessarily drawn to scale.

DETAILED DESCRIPTION OF THE PREFERRED EMBODIMENTS

The present invention is best understood by reference to the detailed figures and description set forth herein.

Embodiments of the invention are discussed below with reference to the Figures. However, those skilled in the art will readily appreciate that the detailed description given herein with respect to these figures is for explanatory purposes as the invention extends beyond these limited embodiments. For example, it should be appreciated that those skilled in the art will, in light of the teachings of the present invention, recognize a multiplicity of alternate and suitable approaches, depending upon the needs of the particular application, to implement the functionality of any given detail described herein, beyond the particular implementation choices in the following embodiments described and shown. That is, there are numerous modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

The present invention will now be described in detail with reference to embodiments thereof as illustrated in the accompanying drawings.

Detailed descriptions of the preferred embodiments are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

It is to be understood that any exact measurements/dimensions or particular construction materials indicated herein are solely provided as examples of suitable configurations and are not intended to be limiting in any way. Depending on the needs of the particular application, those skilled in the art will readily recognize, in light of the following teachings, a multiplicity of suitable alternative implementation details.

One aspect of the present invention is the of identifying and solving problems attendant to prior art approaches is to discover approaches that more optimally achieve a very difficult balance between the competing properties of sufficient strength and sufficient radiolucent properties. Preferred embodiments of the present invention provide means for shoulder migration during radiography that alleviate line of sight overlayment of the vertebral structures while maintaining sufficient strength to exert the motive force necessary to migrate the shoulders. Preferred embodiments are implemented without a carbon/glue interface, which directly overlays the lower cervical vertebral bodies in the prior art. Preferred embodiments also provide density reduction to all structures of the shoulder pusher as compared to the prior art.

FIG. 2 is a diagrammatic side view of an exemplary shoulder pusher 200, in accordance with an embodiment of the present invention. In the present embodiment, shoulder pusher 200 comprises an arch 203 and a pusher tube 205 similar to shoulder pusher 100 shown by way of example in FIG. 1. However, pusher tube 205 in shoulder pusher 200 is asymmetrically positioned at the lower portion of arch 203 as opposed to bisecting the arch from a straight position, as in the prior art. This generally eliminates the direct line of sight overlayment of the vertebral column by pusher tube 205 as viewed laterally.

In order to further alleviate any artifact introduced into the radiographic visualization of the cervical vertebral column, shoulder pusher 200 incorporates a method to reduce the density in the construction of arch 203 in portions where arch 203 directly overlays the radiographic line of sight of the vertebral column when viewed laterally. In many practical applications, this is achieved via elimination and replacement of the tube component and accompanying carbon/glue interface to the arch portion with a single unified composition planar sheet of radiolucent material as evidenced in 300,303, and 305, to include, without limitation, Carbon Fiber, PEEK, Beryllium, Glass Fiber Reinforced Acrylic, Thermoplastucs, Polycarbonates, Polyketones, and any other such compositions as prove amenable to usage in Rigid Radiolucent Positioning.

In the present embodiment, arch 203 comprises an advanced curvilinear design employing eccentric geometry in order to further reduce density as much as possible. This eccentric geometry uses segments of circles with different centers to create arch 203, rather than an arch that is a composed of a single circle segment with a single center point. Incorporating what may be thought of by analogy to a "Stealth Technology", this variable density curvilinear architecture is constructed so as to present the thinnest portions of the planar segment to the lateral radiographic view of the cervical vertebral structures, while concurrently widening in the portions outside of the critical beam path, thus distributing the acceptable force load evenly across the shoulders as they are migrated temporarily via the application of distal motive force by the hand-held operator. Additionally, the present embodiment eliminates the carbon/glue plug as a means of fixating the various portions, and instead fashions the entirety of the portions into a one piece composition as referenced above. It is important that strength be preserved in this more gracile design, while simultaneously preserving sufficient thickness so as to not cause overt of pressure to the subject's shoulders during the application of motive force. As previously stated, the original conception of the shoulder pusher arch according to the prior art calls for uniform thickness and density in order to insure strength of the essentially brittle material. Instead, shoulder pusher 200 comprises a thin, radiolucently invisible buttress 207 attached to the top of the thin, eccentric, curvilinear arch 203 for purposes of strength and stability. The present embodiment may also comprise an ergonomic handgrip at the end of pusher tube 205 away from arch 203 for the operator to hold during use. Shoulder pusher 200 is preferably made of carbon fiber; however, other radiolucent materials may be used such as, but not limited to Carbon Fiber, PEEK, Beryllium, Glass Fiber Reinforced Acrylic, Thermoplastics, Polycarbonates, Polyketones, and any other such compositions as prove amenable to usage in Rigid Radiolucent Positioning, etc. Clinical trials of shoulder pushers according to the present embodiment have resulted in vast improvements in radiographic results as artifact is significantly reduced.

The construction and manufacture of the embodiment illustrated by way of example in FIG. 2 relies upon glue to join the disparate parts of complex arch 203. Preferred embodiments of the present invention seek to generally eliminate any inherent weaknesses while concurrently seeking to reduce any and all artifact to virtually non-existent levels with the ultimate goal of producing a virtually invisible and virtually indestructible radiolucent arch. Buttress 207 is focused on for optimization to improve the entire design via an increase of strength and radiolucent properties since buttress 207 is the main load bearing component of shoulder pusher 200 and the most radiolucent component. Preferred embodiments extend the buttress to create the main body of the shoulder pusher as a one-piece structure to provide strength and to eliminate glue interfaces which may produce artifact.

FIGS. 3A, 3B and 3C illustrate an exemplary one-piece shoulder pusher 300, in accordance with an embodiment of the present invention. FIG. 3A is a diagrammatic side view. FIG. 3B is a diagrammatic top view, and FIG. 3C is a diagrammatic front view. In the present embodiment, shoulder pusher 300 is a one-piece anatomic radiolucent positioning device of variable density comprising a variable width radiolucent arch 303 formed at the terminus of an asymmetrically offset tapered arm 305 of radiolucent sheeting. In the present embodiment, shoulder pusher 300 is preferably made of carbon; however, alternate embodiments may be made of various different radiolucent materials such as, but not limited to, Carbon Fiber, PEEK, Beryllium, Glass Fiber Reinforced Acrylic, Thermoplastics, Polycarbonates, Polyketones, and any other such compositions as prove amenable to usage in Rigid Radiolucent Positioning, etc. In the present embodiment, tapered arm 305 is asymmetrically positioned at the lower portion of arch 303 and is slightly angled. This positioning of tapered arm 305 generally eliminates artifact caused by the shoulder pusher directly overlaying the vertebral column when in use, as in the prior art, while still enabling an operator to transmit the necessary motive force to migrate the shoulders. Alternate embodiments may be implemented where the tapered arm is positioned at the top of the arch. In the present embodiment, the reduced density of the thin yet strong combination of all of the radiolucent structures into one low density sheet renders shoulder pusher 300 virtually free of artifact.

Referring to FIGS. 3B and 3C, the thickness of shoulder pusher 300 varies throughout its structure. This enables the density of shoulder pusher 300 to be lower over key anatomical features to be visualized while still preserving the mechanical integrity necessary to efficiently and comfortably migrate the shoulders. For example, without limitation, a middle portion 311 of arch 303 is thinner than outer portions 313. This enables arch 303 to be thick enough where needed to comfortably migrate a subject's shoulders without the excessive pressure that would be caused by a uniformly thin arch while providing low density in the area over the cervical vertebrae. Those skilled in the art, in light of the present teachings, will readily recognize that the variance in density of the structure of the shoulder pusher may be different in alternate embodiments. For example, without limitation, one alternate embodiment may have a uniform thin density except for a thickened edge, similar to a lip, along the arch where the shoulder pusher comes into contact with the subject. Some embodiments may be implemented to view specific portions of the subject's anatomy; for example, without limitation, one such embodiment may have a thicker density near the arch and a lower density away from the arch in order to obtain radiographic images of the higher cervical vertebrae. Some embodiments may include padding along the edge of the arch for the comfort of the subject.

In the present embodiment, arch 303 has an eccentric curvilinear design that also contributes to the low density of shoulder pusher 300. Alternate embodiments of the present invention may have eccentric arches of various different shapes and sizes to accommodate a variety of subjects, such that the density reduction methodologies described herein may be applied to various anatomical structures outside of the cervical vertebral bodies, while still utilizing the single piece planar composition of radiolucent material combined with the eccentric geometry of the variable density arch. One practical embodiment of the variable density arch employs variation in the structural geometry of the arch itself in order to minimize radiographic artifact while still preserving crucial structural strength and integrity. The geometry principles taught by way of example can readily be applied to other portions of the anatomy with relatively strait forward modifications specific to the structures needing to be visualized radiographically. Furthermore some alternate embodiments may be implemented without an eccentric arch, but with a variable density, eccentric curvilinear segments of polygon which most specifically attend to the essential requirements of radiographic visualization. The polygons by way of example, without limitation, may include ovals, triangles, trapezoids, etc. with usage of the variable density/variable geometric components and methods as described herein as regards to the arch. In the present embodiment, shoulder pusher 300 comprises attachment means 309 for a connection tube, a handle, a table mount, or other such equipment that aids in the use of shoulder pusher 300.

In typical use of the present embodiment, two shoulder pushers 300 are used to migrate the shoulders of a subject during a radiographic procedure. Some procedures may only require the use of one shoulder pusher 300 to migrate one shoulder. In cases where two shoulder pushers 300 are used, shoulder pushers 300 may be coupled together, for example, without limitation, with an adjustable connecting tube, as shown by way of example in FIG. 1. Shoulder pusher 300 is typically used to migrate the shoulders of a subject toward the subject's feet in a pushing mode. In the pushing mode, arch 303 of shoulder pusher 300 is placed on the subject's shoulder and an operator pushes shoulder pusher into the subject's shoulder in order to cause the shoulder to migrate toward the subject's feet. Once the procedure is complete, the operator releases shoulder pusher 300 from the subject's shoulder, and the shoulder returns to its natural position. In the present embodiment, shoulder pusher 300 not only has utility in the pushing mode but also in a pulling mode and an encircling mode for various usages where radiographic anatomical positioning may be necessary for example, without limitation, MRI compatible anatomic limb positioning, Scoliosis positioning, diagnostic positioning, etc. In the pulling mode, whereas the would be fashioned so as to transmit proximal migratory pressure for purposes of rigid radiolucent positioning, the unified composition could be altered slightly while simultaneously making full usage of the density reduction methodology herein described. in the pulling modality, the present arch would be constructed so as to reverse the direction of the arch such that in the hand held or table mounted functions, the method of the variable density/variable geometry arch could pull as opposed to push the shoulders with attachment points to a Patient Positioning Platform, which, in many practical applications, could be of significant clinical and diagnostic value as regards Radiography for Emergent Trauma in the E.R. In the encircling mode, whereas the present arch would be fashioned to work in tandem so as to encircle limbs, etc. for purposes of rigid radiolucent positioning of limbs, etc, during intra-operative and diagnostic procedures incorporating Radiography, MRI and CT Scanning, the unified composition could be altered slightly while simultaneously making full usage of the density reduction methodology herein described. it should be noted that in the encircling modality it is contemplated that the present arch would have practical value and implementations as a limb/anatomical positioner in the clinical/surgical/diagnostic settings of the, without limitation, MRI/CT and other emerging imaging environments, where the method and discipline of rigid radiolucent positioning is being pioneered and made possible by the present embodiment of the arch method of mechanically usable/viable density reduction of radiolucent structures. A multiplicity of alternative usages of the present arch embodiment as a lateral anatomic rigid radiolucent positioner for clinical/diagnostic/surgical settings will be readily apparent to those skilled in the art in light of the teaching of the present invention. Examples of which include, without limitation, spinal and hip positioners for usage during surgery to correct for scoliosis, possible usage for pinpoint mammography, head positioners (halos) which would capture and gently fixate the patients head in encircling radiolucent arches without resort to percutaneous pin fixation thru the patients skin. Testing with shoulder pusher 300 has shown near total elimination of all density artifact such that the usage of shoulder pusher 300 appears to occur almost invisibly. Shoulder pusher 300 also exhibits tremendous strength of design, such that a pair of shoulder pushers according to the present embodiment can withstand load bearing of weight up to and beyond 1200 pounds.

The embodiments illustrated and described in the foregoing are hand-held, manually operated devices. However, those skilled in the art, in light of the present teachings, will readily recognize that alternate embodiments may be implemented to be machine operated or otherwise automated. For example, without limitation, one such embodiment may comprise a shoulder pusher that is coupled to a table and operated with a hand crank or ratchet, or that is hand operated yet locks unidirectionally when released, so as to not expose a hand held operator to radiation. Other automated embodiments may be motorized or operated by pneumatics or hydraulics.

It will be further readily apparent to those skilled in the art, in light of the teaching of the present invention, that the foregoing embodiments may be readily configured, depending upon the needs of the particular application, to work as a scoliosis positioner in pushing mode with attachment points to the patient positioning platform for purposes of directing motive force against the Hips and trunk of the patient . . . as a limb positioner in encircling mode with 2 variable density/variable geometry arches facing one another and adjusted and locked via a locking pin at the lower portions. As a suspected subluxation visualizer in the pulling mode with attachment points to a Patient positioning Platform for purposes of migrating the shoulders while NOT interfering with the Foam Stabilizers placed around the Neck for purposes of Fixating a suspected Neck Breakage. in addition to shoulder pushing/pulling, as well as the imaging compatible limb positioners as described. A multiplicity of alternative applications of the present arch as a lateral anatomic rigid radiolucent positioner for clinical/diagnostic/surgical settings will be obvious to those skilled in the art. Examples of which include, without limitation, spinal and hip positioners for usage during surgery to correct for scoliosis, possible usage for pinpoint mammography, head positioners (halos) which would capture and gently fixate the patients head in encircling radiolucent arches without resort to percutaneous pin fixation thru the patients skin. A multiplicity of alternative usages as rigid radiolucent positioners is possible for use throughout the anatomy.

Having fully described at least one embodiment of the present invention, other equivalent or alternative methods of providing a rigid radiolucent anatomic positioning device according to the present invention will be apparent to those skilled in the art. The invention has been described above by way of illustration, and the specific embodiments disclosed are not intended to limit the invention to the particular forms disclosed. For example, the particular implementation of the shoulder pusher may vary depending upon the particular type of material used. The shoulder pushers described in the foregoing were directed to radiolucent implementations; however, similar techniques are to provide shoulder pushers that are made of materials that are not radiolucent such as, but not limited to, plastic or metal for purposes other than radiography, for example, without limitation, holding a subject' shoulders stationary during other types of procedures or while transporting the subject. Non-radiolucent implementations of the present invention are contemplated as within the scope of the present invention. The invention is thus to cover all modifications, equivalents, and alternatives falling within the spirit and scope of the following claims.

Claim elements and steps herein have been numbered and/or lettered solely as an aid in readability and understanding. As such, the numbering and lettering in itself is not intended to and should not be taken to indicate the ordering of elements and/or steps in the claims.

What is claimed is:

1. An apparatus comprising:
first means for migrating a first anatomic part, said first means for migrating comprising:
first means for applying a motive force; and
first means for contacting the first anatomic part, wherein said first means for contacting is located at a distal end of said first means for applying and is asymmetrically offset from said first means for applying, and said first means for contacting further comprises a variable density comprising a variable width.

2. The apparatus as recited in claim 1, further comprising means for strengthening an upper portion of said first means for contacting.

3. The apparatus as recited in claim 1, further comprising first means for joining said first means for migrating to an equipment that aids in the use of said first means for migrating.

4. The apparatus as recited in claim 3, further comprising:
second means for migrating a second anatomic part, said second means for migrating comprising:
second means for applying a motive force; and
second means, for contacting the second anatomic part, wherein said second means for contacting is located at a distal end of said second means for applying and is asymmetrically offset from said second means for applying; and
second attachment means for joining said second means for migrating to the equipment.

5. An apparatus comprising:
a first anatomic positioner for migrating a first anatomic part, said first anatomic positioner comprising:
a first tapered arm for applying a motive force; and
a first arch at a distal end of said first tapered arm for contacting the first anatomic part, said first arch comprising a variable density comprising a variable width where said first arch is asymmetrically offset from said first tapered arm such that a longitudinal axis of said first tapered arm extends through a lower portion of said first arch.

6. The apparatus as recited in claim 5, further comprising a thin buttress extending from a top of said first tapered arm to an upper portion of said first arch for strengthening said upper portion.

7. The apparatus as recited in claim 5, wherein a middle portion of said first arch is thinner than outer portions.

8. The apparatus as recited in claim 5, wherein said first arch comprises an eccentric curvilinear shape.

9. The apparatus as recited in claim 6, wherein a portion of said top of said first tapered arm is below a center line bisecting said first arch.

10. The apparatus as recited in claim 5, wherein said first anatomic positioner is a one-piece radiolucent structure.

11. The apparatus as recited in claim 5, further comprising first means for joining said first anatomic positioner to an equipment that aids in the use of said first anatomic positioner.

12. The apparatus as recited in claim 11, further comprising:
a cross-bar comprising a first end and a second end wherein said first end is joined to said first means for joining;
a second anatomic positioner for migrating a second anatomic part, said second anatomic positioner comprising:
a second tapered arm for applying a motive force; and
a second arch at a distal end of said second tapered arm for contacting the second anatomic part, said second arch comprising a varying width and a varying density where said second arch is asymmetrically offset from said second tapered arm such that a longitudinal axis of said second tapered arm extends through a lower portion of said second arch; and
second attachment means for joining said second anatomic positioner to said second end.

13. A method of using the apparatus of claim 12 wherein said first and second anatomic parts are human shoulders, the method comprising the steps of:
joining said first anatomic positioner to a first end of a cross-bar; and
joining a second anatomic positioner to said second end of said cross-bar.

14. The method of claim 13, further comprising the step of positioning said first or second anatomic positioners into suitable alignment with the shoulders of a person to enable migration towards the patient's feet of at least one shoulder by properly pushing said anatomic positioner(s) onto the shoulder.

15. The method of claim 13, further comprising the step of configuring at least one of said anatomic positioners into a pulling mode to enable migration away from the patient's feet of at least one shoulder by properly pulling the at least one shoulder using said at least one anatomic positioner.

16. A method comprising the steps of:
forming a first tapered arm for applying a motive force to migrate a shoulder; and
forming a first arch at a first end of said first tapered arm for contacting the shoulder, said first arch comprising a variable density comprising a variable width where said first arch is asymmetrically offset from said first tapered arm such that a longitudinal axis of said first tapered arm extends through a lower portion of said first arch.

17. The method as recited in claim 16, further comprising the step of forming a thin buttress extending from a top of said first tapered arm to an upper portion of said first arch for strengthening said upper portion.

18. The method as recited in claim 17, wherein a portion of said top of said tapered arm is below a center line bisecting said first arch.

19. The method as recited in claim 16, further comprising the step of joining first means for attaching to a second end of said first tapered arm to an equipment that aids in the migrating of the shoulder.

20. The method as recited in claim 19, further comprising the steps of:
   fabricating a length adjustable cross-bar for joining a first end of said cross-bar to said first means for attaching;
   forming a second tapered arm for applying a motive force to migrate a shoulder;
   forming a second arch at a first distal end of said second tapered arm for contacting the shoulder, said second arch comprising a varying width and a varying density where said second arch is asymmetrically offset from said second tapered arm such that a longitudinal axis of said second tapered arm extends through a lower portion of said second arch; and
   joining a second means for attaching to a second end of said second tapered arm for joining a second end of said cross-bar to said second means for attaching.

21. The method as recited in claim 16, wherein said first tapered arm and said first arch are formed as a one-piece radiolucent structure.

22. The method as recited in claim 16, wherein a middle portion of said first arch is thinner than outer portions.

23. The method as recited in claim 16, wherein said first arch comprises an eccentric curvilinear shape.

* * * * *